US011298150B2

(12) United States Patent
Regensburger et al.

(10) Patent No.: US 11,298,150 B2
(45) Date of Patent: Apr. 12, 2022

(54) POSITIONING UNIT WITH A PLURALITY OF INDICATORS FOR GUIDING A NEEDLE

(71) Applicant: Siemens Healthcare GmbH, Erlangen (DE)

(72) Inventors: Alois Regensburger, Erlangen (DE); Heiko Mehldau, Nuremberg (DE); Amilcar Alzaga, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 46 days.

(21) Appl. No.: 16/871,023

(22) Filed: May 10, 2020

(65) Prior Publication Data

US 2020/0352592 A1 Nov. 12, 2020

(30) Foreign Application Priority Data

May 10, 2019 (DE) .......................... 102019206825.1

(51) Int. Cl.
*A61B 17/34* (2006.01)
*A61B 90/13* (2016.01)
*A61B 90/30* (2016.01)

(52) U.S. Cl.
CPC .......... *A61B 17/3403* (2013.01); *A61B 90/13* (2016.02); *A61B 2017/3405* (2013.01); *A61B 2090/309* (2016.02)

(58) Field of Classification Search
CPC ..... A61B 17/3403; A61B 90/11; A61B 90/13; A61B 2017/3405–3409; A61B 2090/309;
(Continued)

(56) References Cited

U.S. PATENT DOCUMENTS 6,400,979 B1 * 6/2002 Stoianovici ............ A61B 90/36
600/427
7,494,494 B2 * 2/2009 Stoianovici ............ A61B 90/50
600/566
(Continued)

FOREIGN PATENT DOCUMENTS

CN 103211654 A 7/2013
CN 205458954 U 8/2016
(Continued)

OTHER PUBLICATIONS

German Office Action for German Application No. 10 2019 206 825.1 dated Jan. 30, 2020, with English translation.
(Continued)

*Primary Examiner* — Sarah A Simpson
*Assistant Examiner* — Lindsey Bachman
(74) *Attorney, Agent, or Firm* — Lempia Summerfield Katz LLC

(57) ABSTRACT

A positioning unit for guiding a medical object such as a needle includes a securing unit by which the positioning unit may be arranged on the medical object. In order to enable an improved guidance for the medical object, an indicating element with a plurality of indicators is provided. The indicating element is arranged in a fixed position relative to the securing unit. An acquisition unit acquires an item of movement information. The positioning unit is configured to control the plurality of indicators dependent upon the movement information.

20 Claims, 5 Drawing Sheets

(58) Field of Classification Search
CPC .............. A61B 90/10; A61B 2090/101; A61B 2034/2059; A61M 25/0113
See application file for complete search history.

(56) References Cited

U.S. PATENT DOCUMENTS

| | | | |
|---|---|---|---|
| 10,857,005 B2* | 12/2020 | Dassonville | A61B 17/1633 |
| 2004/0152970 A1 | 8/2004 | Hunter | |
| 2010/0312103 A1* | 12/2010 | Gorek | A61B 6/547 |
| | | | 600/425 |
| 2013/0190598 A1 | 7/2013 | Sharonov et al. | |
| 2016/0310165 A1 | 10/2016 | Baldwin | |
| 2017/0238999 A1* | 8/2017 | Lavallee | A61B 34/20 |
| 2018/0228568 A1* | 8/2018 | Kato | A61B 90/11 |
| 2019/0046275 A1 | 2/2019 | Winneberger | |
| 2019/0110846 A1* | 4/2019 | D'Amelio | A61B 34/30 |
| 2021/0161554 A1* | 6/2021 | Stem | A61B 17/3468 |

FOREIGN PATENT DOCUMENTS

| | | | |
|---|---|---|---|
| CN | 106725787 A | 5/2017 | |
| CN | 108309409 A | 7/2018 | |
| CN | 208404768 U | 1/2019 | |
| CN | 109389620 A | 2/2019 | |
| DE | 112008002851 B4 | 6/2018 | |

OTHER PUBLICATIONS

German Decision to Grant for German Application No. 10 2019 206 825.1 dated Mar. 2, 2020, with English translation.
Chinese Office Action for Chinese Application No. 202010376593.7 dated Apr. 22, 2021.

* cited by examiner

POSITIONING UNIT WITH A PLURALITY OF INDICATORS FOR GUIDING A NEEDLE

This application claims the benefit of German Patent Application No. DE 10 2019 206 825.1, filed on May 10, 2019, which is hereby incorporated by reference in its entirety.

BACKGROUND

The present embodiments relate to a positioning unit for guiding a medical object.

In the context of medical treatments, it is often necessary to introduce a medical needle in a targeted manner (e.g., along a precisely specified needle path or a previously planned trajectory) into a medical target object (e.g., a patient or a simulator for simulating the patient). A simulator may also be referred to as a dummy. With the aid of the dummy, the patient or the medical treatment on the patient may be simulated. For example, for a treatment in the interior of the body of the patient (e.g., on internal organs), an exact guidance of the needle along the needle path or the planned trajectory is important. By this, the guidance of the needle along the correct path between tissues and bones and the targeted treatment of the respective organ may be provided. In this context, for example, the monitoring of the introduction of the needle or the insertion process is possible using fluoroscopy. The high loading with X-rays is disadvantageous thereby. Specifically, by guidance of the medical needle along the needle path, it may be provided that the needle reliably reaches a target point within the target object. The target point may be, for example, a previously specified position between bones, for example, for introduction between two intervertebral disks, or a tumor. In the case of a dummy, the bones, and/or the tumor may be simulated by suitable configurations of the dummy.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved guidance for a medical object such as a needle is provided.

A first aspect relates to a positioning unit for guiding a medical object (e.g., a needle) having a securing unit by which the positioning unit may be arranged on the medical object. The positioning unit is distinguished by an indicating element with a plurality of indicators, where the indicating element is arranged in a fixed position relative to the securing unit, and an acquisition unit for acquiring an item of movement information. Thereby, the positioning unit is configured to control the plurality of indicators dependent upon the movement information.

The positioning unit may be arranged on the needle by the securing unit. In other words, the securing unit is configured to arrange the positioning unit on the medical object. For example, the securing unit is configured for force-fitting and/or form-fitting arrangement of the positioning unit on the medical object. The securing unit is thereby configured, for example, to enter into a releasable mechanical connection with the medical object. For this purpose, the securing unit may encompass the medical object completely or partially in order to create the mechanical connection. For example, the securing unit may have a receptacle for at least partial encompassing of the medical object. A fixing element of the securing unit may be configured for mechanically securing the medical object in the receptacle. In specific examples, the securing unit may have a clip mechanism or a screw mechanism.

Using the indicating element, for example, the plurality of indicators have a pre-determined position relative to the securing unit and/or relative to a remaining part of the positioning unit. In general, the indicating element is arranged in the fixed position relative to the securing unit. In other words, the securing unit and the indicating element have a fixed position relative to one another as respective parts of the positioning unit. The plurality of indicators as parts of the indicating element may each have a fixed position relative to a remainder of the indicating element. For example, the indicating element has a support element that is configured to hold the plurality of indicators. The support element may be configured, for example, in a plate-shaped manner. Alternatively or additionally, the holding element may be formed partially as a cylinder or a hollow cylinder.

The plurality of indicating elements may be pointers, blinkers, or lighting devices. For example, the positioning unit is configured to control or to move the plurality of pointers or blinkers dependent upon the movement information. The plurality of pointers or blinkers may be aligned or positioned accordingly.

The acquisition unit may be configured, for example, to receive the movement information via a data connection. For example, the acquisition unit may be configured to receive the movement information from a determining unit that is not part of the positioning unit. Alternatively or additionally, the acquisition unit may be configured for receiving the movement information from a determining unit arranged on the positioning unit. The determining unit is described in greater detail below. The movement information may specify, for example, the direction in which the positioning unit may be moved in order to reach a target position. The target position may correspond, for example, to a position along a pre-determined trajectory for the medical object. For example, the movement information specifies the direction in which the positioning unit is to be moved in order to guide the medical object along the pre-determined trajectory.

The plurality of indicators are controllable dependent upon the movement information. For example, the positioning unit is configured to visualize the movement information using the plurality of indicators. It may be visualized, for example, by the plurality of indicators, the direction in which the positioning unit is to be turned or tilted or moved.

For example, it may be provided that the positioning unit acquires the movement information using the acquisition unit. The acquisition unit may be, for example, a radio receiver. The movement information specifies the direction in which the positioning unit is to be moved. Through visualization of the movement information by the plurality of indicators, the positioning unit may then be positioned as specified by the movement information and, for example, along a pre-determined trajectory.

According to one development, the plurality of indicators are each configured as lighting devices (e.g., light-emitting diodes). In other words, the positioning unit may have a plurality of lighting devices or light-emitting diodes as the plurality of indicators. Light-emitting diodes may be configured to be particularly energy-saving and compact so that a compact design of the positioning unit is enabled. For example, the positioning unit is configured to control the plurality of lighting devices dependent upon the movement information. For example, the positioning unit is configured to visualize the movement information using the plurality of lighting devices. During the controlling or the visualization, a light pattern corresponding to the movement information may be generated or radiated.

According to one development, it is provided that the plurality of indicators are arranged such that the plurality of indicators lie on a same circle or a same envelope surface of a cylinder. In other words, the plurality of indicators may all be arranged on a circle. For example, at least three (e.g., exactly four) indicators are arranged on a circle. Alternatively, the plurality of indicators may all be arranged on a plurality of circles. In this case, at least three (e.g., exactly four) of the plurality of indicators are arranged on each of the circles. If the plurality of circles each have the same radius and only one axial displacement relative to one another, the indicators that are arranged on different circles are arranged on the same envelope surface of a cylinder. Respective circular planes of the plurality of circles extend, for example, parallel to one another. Overall, through the aforementioned arrangement, an advantageous visualization of the movement information is enabled.

According to one development, the securing unit is configured to arrange the positioning unit on the medical object such that a line of gravity that extends along a main extent of the medical object extends through the midpoint of the circle or the envelope surface. In other words, the securing unit is configured to arrange the positioning unit on the medical object such that the circle or the envelope surface, on which the plurality of indicators are arranged, encompass the medical object (e.g., a main extent direction). In this encompassing, the line of gravity of the medical object extends through the midpoint of the circle or the envelope surface. The expression of the midpoint of the envelope surface denotes herein a point on the rotationally symmetrical axis of the cylinder. The cylinder and the envelope surface of the cylinder do not have to be physically present. In other words, the envelope surface or the cylinder may be an imaginary geometrical object in order to describe the geometry of the plurality of indicators. Through the arrangement of the plurality of indicators around the central line of gravity of the medical object, a particularly intuitive guidance of the positioning unit may be enabled.

According to a further development, two adjacent items of the plurality of indicators that are arranged together on the circle or on the cylinder each have an even spacing from one another in the peripheral direction. In other words, the items of the plurality of indicators arranged on a common circle are evenly distributed over the circle. By this, all the indicators arranged on the circle have the same spacing from the respective adjacent indicators on the same circle. By this geometric embodiment of the positioning unit, a further improvement may be achieved in the guidance of the positioning unit and thus of the medical object.

It is further provided that the indicating element includes two (e.g., round) plates that may each be arranged using a respective part of the securing unit independently of one another. On each of the two plates, at least three (e.g., four) of the plurality of indicators are arranged. For example, the two plates may be arranged on the medical object, by the securing unit, in a different longitudinal position in relation to the main extent direction of the medical object. Thereby, the securing unit is configured, for example, to arrange the two plates in relation to the medical object such that the line of gravity extends through a respective midpoint of the plates. In some exemplary embodiments, the two plates have no mechanical connection to one another. In this case, the relative positioning to one another is only fixed by the arrangement of both plates to the medical object. In other words, the two plates may be connected to one another indirectly by the medical object if both plates are arranged on the medical object. The securing unit may have two subelements, where each of the subelements is arranged on one of the two plates. In other words, each plate has a respective subelement of the securing unit. Each subelement arranged on a plate may be configured to arrange the respective plate on the medical object. In this way, the positioning unit may be configured to be particularly simple and compact.

According to one development, the indicating unit has a plurality of linear lights, where the plurality of indicators are part of the linear lights, and the securing unit is configured to arrange the positioning unit on the medical object such that the plurality of linear lights extend parallel to the main extent of the medical object. The plurality of linear lights may be configured to visualize the direction in which different regions of the positioning unit are to move according to the movement information. In this way, it may be indicated, for different regions of the positioning unit, the regions in which a movement is to take place.

According to one development, the positioning unit is configured, through suitable control of the plurality of indicators, to indicate the direction in which the positioning unit is to be turned and/or moved according to the movement information. In other words, the positioning unit is configured to visualize the movement information in that the plurality of indicators are controlled correspondingly. The corresponding controlling may include, for example, the representation of a light pattern. In this case, the movement information may be visualizable by the light pattern. The light pattern, for example, may be static or change over time. For example, the light pattern includes the switching on, switching off, dimming or blinking of the plurality of indicators. In the case of a blinking, the movement information may be at least partially visualized by the corresponding blinking pattern (e.g., the temporal pattern of the blinking of the corresponding indicators). Alternatively or additionally, the light pattern may include that the plurality of indicators are controlled for radiating light of a respective color. The respective color of different items of the plurality of indicators may be different thereby. For example, the plurality of indicators are controlled in the context of the controlling dependent upon the respective position relative to the pre-determined trajectory for the medical object. In other words, the positioning unit may be configured to control each indicator of the plurality of indicators individually, dependent upon the respective position of the relevant indicators relative to the pre-determined trajectory for the medical object. Thereby, the positioning unit may be configured, dependent upon the respective position for each indicator of the plurality of indicators, to specify a respective light pattern. Overall, thereby, the movement information may be advantageously visualized.

According to one development, the positioning unit is configured to indicate, in a first illumination step, the direction in which the positioning unit is to be turned according to the movement information, and in a second illumination step, to indicate the direction in which the positioning unit is to be moved according to the movement information. The first illumination step and the second illumination step follow one another. For example, the first illumination step may take place before the second illumination step, or the second illumination step may take place before the first illumination step. Therein, the indication of the direction in which the positioning unit is to be turned may be at least partially shown with the same of the plurality of indicators as the indication of the direction in which the positioning unit is to be moved. "Turning" may herein be, for example, a rotary movement. "Movement" may be, for example, a translational position change. In other words, the first illumination step may relate exclusively to the rotation, and the second illumination step may relate exclusively to the translation of the positioning unit. For example, it is provided that the positioning unit is configured, in the first illumination step, to indicate exclusively the direction in which the positioning unit is to be turned and/or rotated according to the movement information. For example, the positioning unit is configured, in the second illumination step, to indicate exclusively the direction in which the positioning unit is to be moved and/or translationally moved according to the movement information. The positioning unit may thereby be configured to carry out the indication according to the first illumination step and the second illumination step partially or entirely by the same of the plurality of indicators. In this way, the number of indicators needed for this may be reduced.

According to one development, the positioning unit is configured, through suitable control of the plurality of indicators, to indicate simultaneously for at least two sub-regions along the main extent direction of the positioning unit the direction in which the relevant subregions of the at least two subregions is to be turned and/or moved according to the movement information. In other words, it is provided that a first part of the plurality of indicators is assigned to a first of the at least two subregions, and a second part of the plurality of indicators is assigned to a second of the at least two subregions. The positioning unit may then be configured to control the first part of the indicators, such that the first part of the indicators indicates the direction in which the first subregion is to be turned and/or to moved. In this example, the positioning unit is additionally configured to control the second part of the plurality of indicators simultaneously, such that the second part of the plurality of indicators indicates the direction in which the second subregion is to turn and/or to move. In other words, it is simultaneously indicated by the first part and the second part of the indicators the direction in which the first subregion and/or the second subregion is to be turned and/or moved. In other words, it is simultaneously indicated for the at least two subregions the direction in which the at least two subregions are to be moved translationally and/or rotationally. Using the indication of the corresponding translational and/or rotational movement for at least two subregions simultaneously, the positioning and/or movement of the positioning unit may be stated and/or indicated for all the degrees of freedom simultaneously.

A second aspect relates to a positioning system with the positioning unit according to the present embodiments, a sensor unit configured to acquire a position and/or orientation of the positioning unit, and a determining unit for determining the movement information dependent upon the acquired position and/or orientation of the positioning unit and a target position.

The sensor unit may be arranged partially or entirely on the positioning unit. The determining unit may be arranged entirely or partially on the positioning unit. Alternatively, the sensor unit and/or the determining unit may be arranged by the positioning unit in an at least partially manual manner. In other words, the positioning unit may be movable relative to the sensor unit or a part of the sensor unit. For example, the positioning unit may be movable relative to the determining unit or to a part of the determining unit. For example, the positioning unit is configured as a hand-held device. The sensor unit and/or the determining unit may be arranged at least partially immovably in a treatment room. For example, the sensor unit and/or the determining unit may at least partially be arranged on a patient support (e.g., an operating table or a bed). In other words, during a proper operation of the positioning system, the sensor unit and/or the determining unit are arranged on the patient support. In some embodiments, the sensor unit and the determining unit may have a common housing. This common housing may be able to be arranged, for example, on the patient support. In some embodiments, the sensor unit and/or the determining unit are each located completely removed from the positioning unit. For example, the sensor unit and/or the determining unit may each be arranged entirely on the patient support and during a proper operation of the positioning system, are arranged on the patient support. The patient support may be configured for holding or for mechanical accommodation of a medical target object.

The determining unit may have an interface for receiving the target position. The target position is, for example, the pre-determined needle path or the pre-determined or planned trajectory. The determining unit may be configured to receive the target position via the interface from a further medical system (e.g., a computed tomography device or an X-ray device). Alternatively or additionally, the determining unit may have a storage device (e.g., a Flash memory, a magnetic memory, or a working memory) for storing the target position.

In the determining unit, a pre-determined rule may be storable or stored. The pre-determined rule states how the movement information is to be determined, dependent upon the acquired position and/or orientation of the positioning unit and the target position. For example, the pre-determined rule may include a mathematical formula and/or an allocation table. For example, it is provided that the movement information is determined such that during the intended tracking or the intended consideration of the movement information visualized by the positioning unit, the positioning unit is moved in the direction of the target position (e.g., translationally and/or rotationally).

The positioning system may have a registration unit that is configured to acquire the positioning of the positioning unit on the medical object (e.g., the needle). In other words, the registration unit may be configured to determine the position in which the positioning unit is arranged on the medical object. Thereby, for example, the relative position between the medical object and the positioning unit is to be determined. For example, an image or a model of the medical object is stored in the registration unit. For the acquisition of the positioning of the positioning unit on the medical object, an image of the positioning unit and of the medical object may be acquired. For example, the registration unit has a sensor (e.g., a camera) for acquiring the image of the positioning unit and of the medical object. For example, the registration unit may be configured to use the stored image of the medical object together with the acquired image for the acquisition of the positioning of the positioning unit on the medical object.

The sensor unit may include an acceleration sensor that is arranged on the positioning unit. In this case, the sensor unit may be configured to determine the position and/or the orientation of the positioning unit based on the acceleration data of the acceleration sensor. In other words, the sensor unit may be configured to determine the position and/or the orientation of the positioning unit based on the acceleration data, similarly to an odometry. Thereby, the position determination may take place, starting from a reference position, by summation and/or integration of acceleration values contained in the acceleration data. The reference position may be pre-determined, for example, using a holding element that may be arranged on a patient support. The sensor unit may be configured, starting from the reference position, to determine the current position and/or orientation of the positioning unit, starting from the reference position by summing and/or integration of the acceleration values. For example, only the acceleration values that have been acquired since the last removal of the positioning system from the reference position (e.g., the holding element) are thereby summed or integrated. In this way, the position and/or orientation of the positioning unit may be determined in an easy manner.

According to one development, the sensor unit has an ultrasound sensor, a radar sensor, an X-ray sensor, an electromagnetic sensor, or a camera. The sensor unit may be configured, using one or more of the aforementioned sensors, to determine the position of the positioning unit. The camera may be part of an optical tracking system, such as is well known from the prior art. The electromagnetic sensor may be part of an electromagnetic tracking system, such as is well known from the prior art. For example, the one or the plurality of the aforementioned sensors are arranged on the operating table. For example, the one or the plurality of sensors are configured to acquire or determine an image of the positioning unit and, from the image, to determine the position and/or orientation of the positioning unit. The position and/or the orientation of the positioning unit, in this case, may be a relative position with respect to a sensor position of the sensor unit.

A third aspect relates to a medical system including the positioning system according to the present embodiments and a patient support (e.g., an operating table or a bed). The sensor unit and the determining unit are arranged on the patient support, and the positioning unit is freely movable relative to the patient support. The medical system is configured to determine the position of the positioning unit and thus, for example, also the position of the medical object, relative to the patient support. In a further embodiment, the system is also configured to determine the position of the positioning unit and thus, for example, also of the medical object, relative to a target object (e.g., a patient or a dummy for simulating the patient). In this way, using the medical system, the medical object (e.g., the needle) may be guided by the positioning unit along a pre-determined needle path or along a pre-determined trajectory.

A fourth aspect relates to a method for guiding a medical object (e.g., a needle) having the following acts: acquiring an item of movement information relating to a positioning unit arranged on the medical object, by an acquisition unit of the positioning unit, and controlling a plurality of indicators of an indicating element of the positioning unit, dependent upon the movement information.

A further method act may include arranging the positioning unit manually or automatically on the medical object. However, this is optional.

The method according to the present embodiments relates to the positioning unit and the positioning system. Therefore, features and developments that have already been disclosed in relation to the positioning unit or the positioning system apply similarly for the method, and vice versa. For the sake of brevity, the features of the positioning system and of the positioning unit will not be described here again in relation to the method according to the present embodiments.

A further aspect relates to a computer program product with program code configured to carry out the method according to the present embodiments when the computer program product is executed on a computer unit. For example, the computer program product may be configured, on execution in the computer, to cause the computer to carry out the method according to the present embodiments. The computer unit may be, for example, a microcontroller, a processor, or a programmable logic gate array (FPGA).

A further aspect relates to a computer-readable medium on which the aforementioned computer program element according to the present embodiments or the corresponding instructions are stored. The computer-readable medium may be, for example, an optical medium, a flash memory, a hard disk drive, or any other digital memory.

The invention will now be described in greater detail by reference to exemplary embodiments and drawings. The specific exemplary embodiments and the figures are regarded as purely exemplary. Features disclosed below and in the drawings further develop the invention and are disclosed as an optional part of the invention.

DETAILED DESCRIPTION

Figure 1:
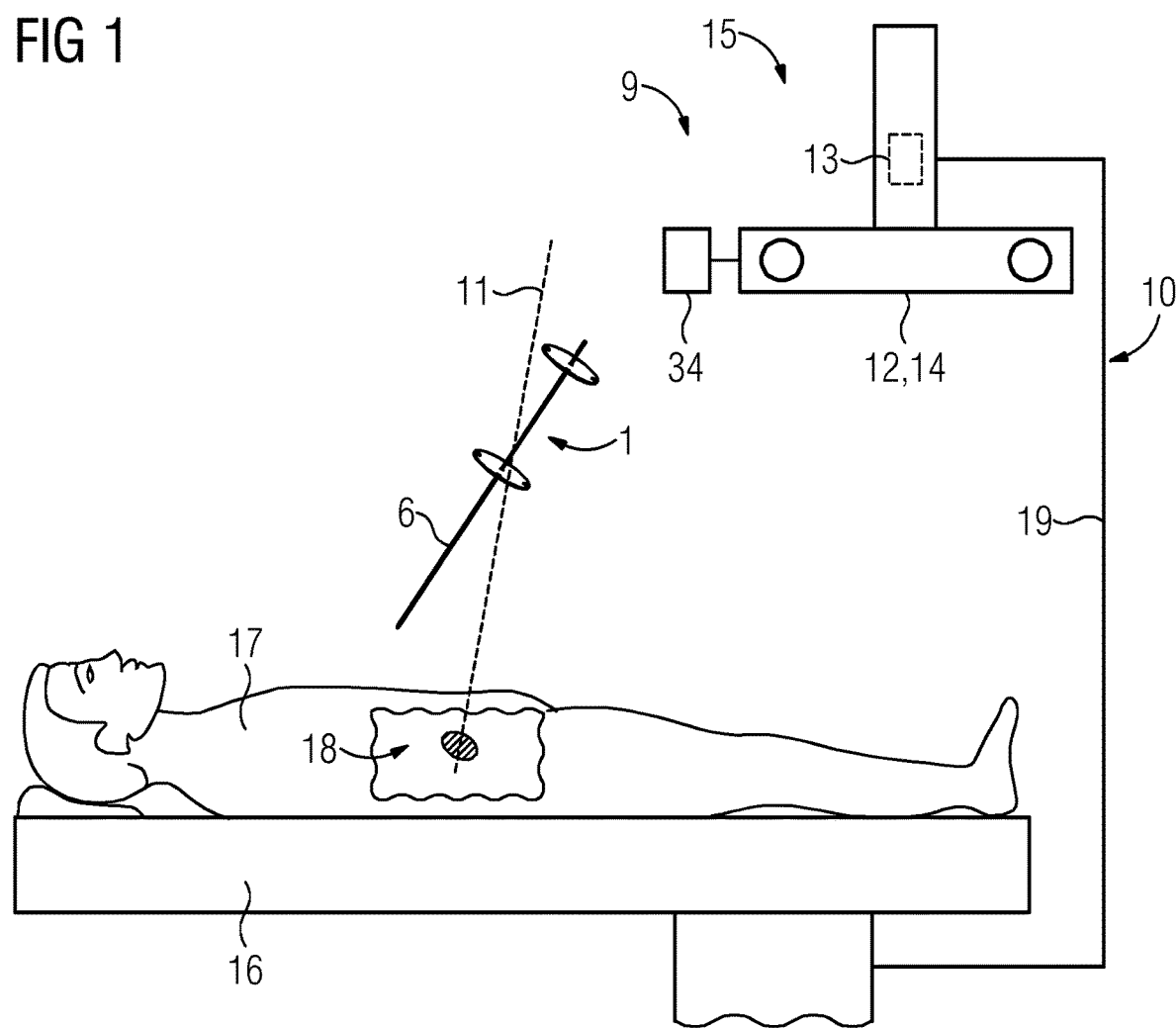
FIG. 1 shows a schematic side view of one embodiment of a medical system with a positioning system.

FIG. 1 shows one embodiment of a medical system 10 that includes a positioning unit 1, a patient support 16, and an immovable module 15. In an intended operating state, the immovable module 15 is arranged, for example, such that the immovable module 15 is immovable relative to the patient support 16. For example, the module 15 is mechanically connected to the patient support 16 by a connecting element 19. The relative position between the module 15 and the patient support 16 is defined by the connecting element 19 and, for example, is constant at least during an operation of the system 10. Alternatively, the immovable module 15 may be arranged in any other way in the pre-determined position relative to the patient support 16. For example, the module 15 is arranged on a wall or a ceiling of a room in which the patient support 16 is located. The patient support 16 may be, for example, an operating table or a hospital bed.

The patient support 16 is configured for holding or receiving a medical target object 17. The medical target object 17 may be a patient or a dummy for simulating the patient. Within the medical target object 17 is a target point 18 to which a medical object 6 is to be guided. For example, the target point is a tumor or a specified position between two bones (e.g., in a joint or on a vertebral column). Thereby, the target point 18 may be simulated by the design of the dummy. In other words, the dummy may simulate bones and tissues of a patient with its design, with a corresponding tumor or corresponding bones.

The medical object 6 is, in the present case, a medical needle. The medical object 6 is to be guided along a pre-determined trajectory 11 (e.g., a previously planned needle path) to a target point 18. In the present case, for the guidance of the needle, a positioning system 9 is provided. The positioning system 9 includes a positioning unit 1 and the immovable module 15.

Figure 2:
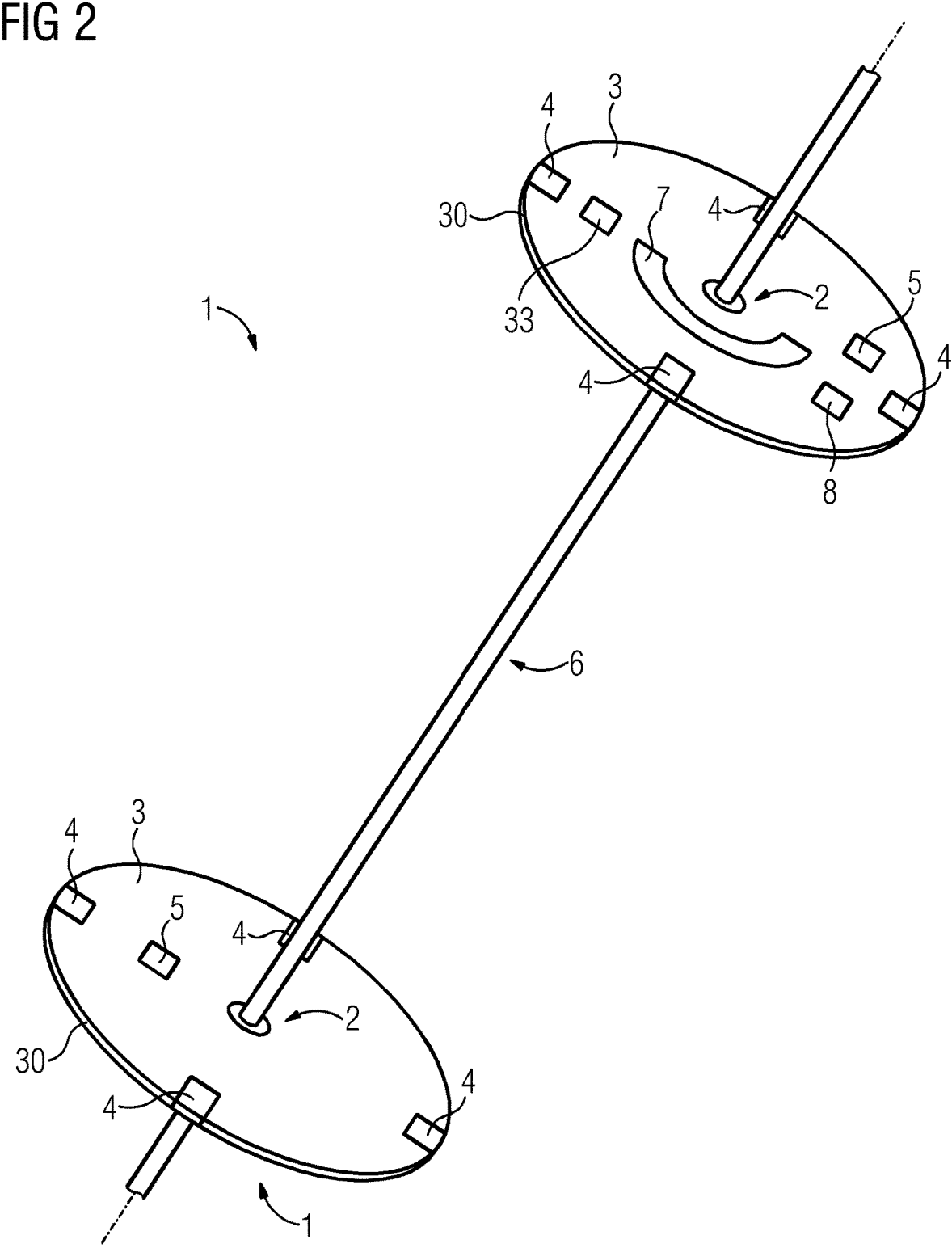
FIG. 2 shows a schematic perspective view of a first embodiment of a positioning unit of the positioning system.
Figure 3:
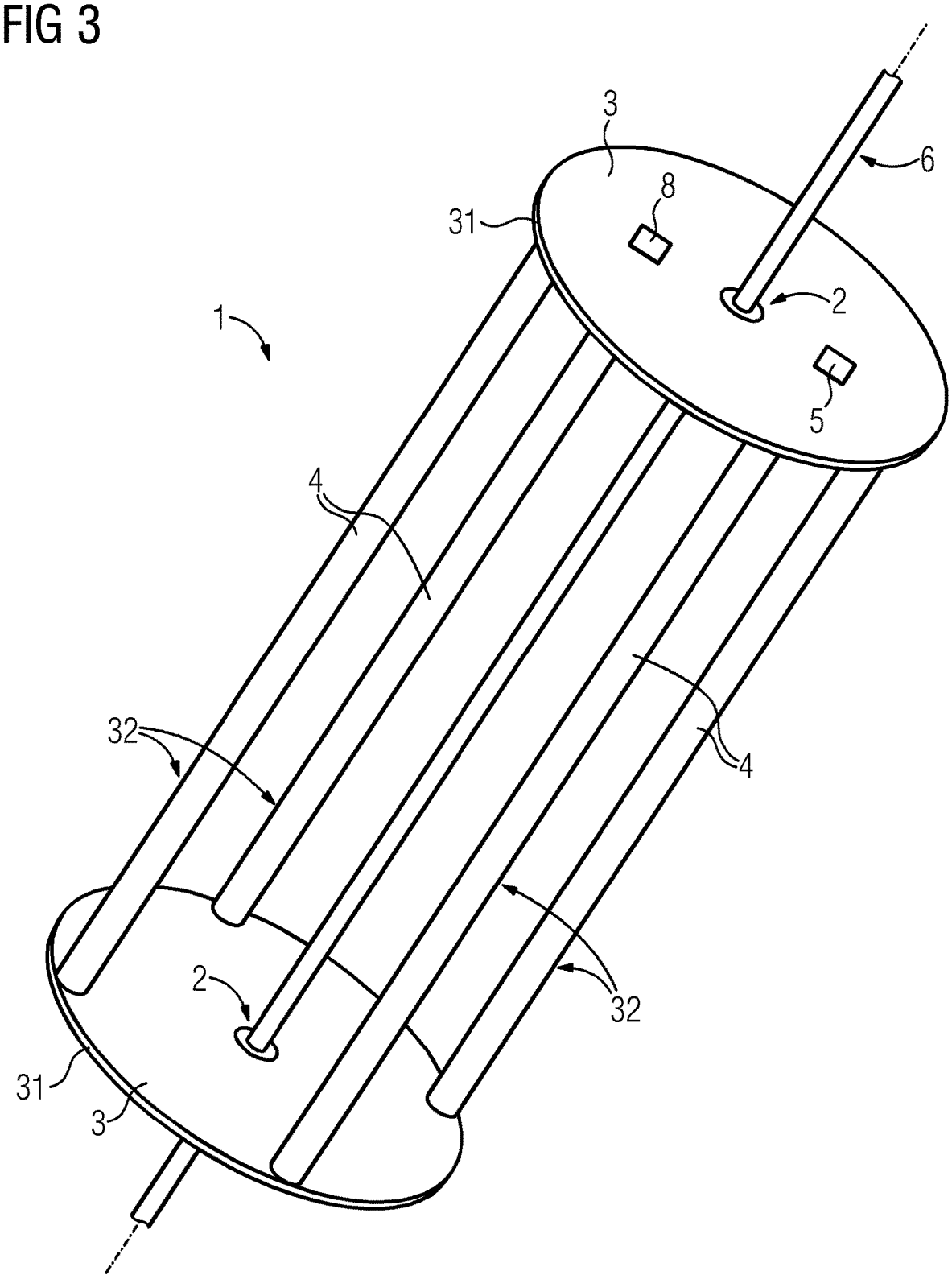
FIG. 3 shows a schematic perspective view of a second embodiment of a positioning unit of the positioning system.

FIG. 2 shows a first exemplary embodiment of the positioning unit 1. FIG. 3 shows a second exemplary embodiment of the positioning unit 1. Common features of both the embodiments will be described. The positioning unit 1 has a securing unit 2 by which the positioning unit 1 may be arranged on the medical object 6 (e.g., a needle). FIGS. 2 and 3 each show the positioning unit 1 in a state arranged on the medical object 6.

For example, the securing unit 2 is configured for force-fitting and/or form-fitting arrangement of the positioning unit 1 on the medical object 6. The securing unit 2 is thereby configured, for example, to enter into a releasable mechanical connection with the medical object 6. In the present case, for this purpose, the securing unit 2 is configured to encompass the medical object entirely or partially in order to create the mechanical connection. For example, the securing unit may have a receptacle for at least partial encompassing of the medical object 6. A fixing element of the securing unit 2 may be configured for mechanically securing or fixing the medical object 6 in the receptacle. In other examples, the securing unit 2 may have a clip mechanism or a screw mechanism.

An acquisition unit 5 of the positioning unit 1 is configured to detect an item of movement information. For example, the acquisition unit 5 is configured to receive the movement information from a determining unit 8, 13. The determining unit 8 may be located partially or entirely in the positioning unit 1. Alternatively or additionally, the determining unit 13 may be located partially or entirely in the immovable module 15. The movement information relates to the positioning of the positioning unit 1 relative to the pre-determined trajectory 11. In that the positioning unit 1 is arranged on the medical object 6, the movement information indirectly also relates to the positioning of the medical object 6 relative to the pre-determined trajectory 11.

The positioning unit 1 has an indicating element 3. The indicating element 3 has a plurality of indicators 4. The indicators 4 may include, for example, lighting devices (e.g., light-emitting diodes). The positioning unit 1 is configured to control the plurality of indicators 4 dependent upon the movement information. Thereby, the movement information is displayed to a user (e.g., a doctor). By displaying the movement information, for example, an item of guidance information is provided for guiding the positioning unit 1 and/or the medical object 6. For example, the positioning unit 1 has a control unit (e.g., a microcontroller or a microprocessor) for controlling the indicators 4 according to the movement information. The control unit may be arranged within the acquisition unit 5.

According to FIG. 2, the indicating element 3 is provided in the form of two round plates 30. The plates 30 are herein not directly connected to one another. For example, the plates 30 are herein exclusively connected indirectly via the medical object 6 when both plates 30 are arranged on the medical object 6. The plates 30 each have a subelement of the securing unit 2, where the plates 30 may each be arranged, by the respective subelement, independently of one another on the medical object 6. In the present case, a plurality of the indicators 4 are arranged on each of the plates 30. For example, at least three indicators 4 are arranged on each of the plates 30. In the present example, four indicators 4 are arranged on each of the plates 30. Both plates 30 may be configured similarly. Alternatively, the plates 30 may also differ from one another. For example, only one of the plates 30 has the determining unit 8. The other of the plates 30 may then be configured to receive the movement information by the acquisition unit 5 from the determining unit 13 of the module 15 or from the determining unit 8 of the other plate 30.

In the present case, the positioning unit 1 also has a light strip 7. The light strip 7 may indicate an orientation of the positioning unit 1. For example, the light strip 7 may be configured to indicate an orientation of the positioning unit 1 relative to the pre-determined trajectory 11. For this purpose, the light strip 7 may be configured to display a pattern that recreates a spirit level. The light strip 7 may indicate that the orientation of the positioning unit 1 corresponds to a desired value when the corresponding plate 30 with which the light strip 7 is associated is oriented perpendicular to the needle path 11 or the trajectory 11. For example, the light strip 7 may visualize the deviation of the orientation from the desired value.

In the exemplary embodiment according to FIG. 2, the positioning unit 1 is configured to represent the movement for both plates 30 simultaneously according to the movement information. Thereby, the two plates are arranged, as shown in FIG. 2, in different subregions of the medical object 6 in relation to a main extent direction of the medical object 6. Thereby, for both subregions, a corresponding movement is visualized. Considered mathematically, in this way, the guidance along the pre-determined trajectory 11 may be unambiguously specified in relation to two different spatial directions, since a straight line is clearly defined by two points. This is described in greater detail below in relation to FIG. 4.

In some embodiments, the positioning unit 1 has only one plate 30. In this case, for example, the combination of the indicators 4 with a light strip 7 is advantageous. In the case of one plate 30, the positioning unit 1 may be configured to display the movement information sequentially. For example, a portion of the movement information that relates to a first spatial direction is firstly visualized, and subsequently, a portion of the movement information that concerns a portion of the movement information that relates to a second spatial direction is visualized. In other words, the first portion of the movement information relates to the first spatial direction, and the second portion of the movement information relates to the second spatial direction. The positioning unit 1 may be configured to control the indicators 4 one after the other according to the first portion and the second portion of the movement information. In this way, the positioning unit 1 may be configured particularly compactly.

According to FIG. 3, a plurality of linear lights 32 is arranged between two plates 31. The linear lights 32 extend thereby from one of the plates 31 to the other of the plates 31. In other words, the linear lights 32 are arranged on both plates 31. The plates 31 may be connected to one another directly by an additional connecting element. Alternatively, apart from the linear lights 32, the plates 32 are connected only indirectly via the medical object 6 when both plates 31 are arranged on the medical object 6. The plurality of indicators 4 are distributed over the linear lights 32. In other words, each of the linear lights 32 has a plurality of indicators 4. The positioning unit 1 has at least three linear lights 32 (e.g., exactly four linear lights 32).

The positioning unit 1 has a sensor unit 33. The sensor unit 33 has, for example, an acceleration sensor. The sensor unit 33 may be configured to determine the position and/or the orientation of the positioning unit based on the acceleration data of the acceleration sensor. In other words, the sensor unit 33 may be configured to determine the position and/or the orientation of the positioning unit similarly to an odometry based on the acceleration data. Thereby, the position determination may take place, starting from a reference position, by summation and/or integration of acceleration values contained in the acceleration data. The reference position may be defined and/or provided, for example, by the immovable module 15 and/or the patient support 16. For example, the immovable module 15 or the patient support 16 has a holding element 34. The holding element 34 may thereby be configured as a base station or a "dock". Using a pre-determined relative position between the reference position and the patient support 16 or the medical target object 17, in this way, the position of the positioning unit 1, and thereby also of the medical object 6, relative to the patient support 16 may be determined. Alternatively or additionally, the sensor unit 33 may have a camera, a radar sensor, or an ultrasonic sensor for navigation in the space.

The determining unit 8 may be configured to determine the movement information dependent upon the relative position that is acquired by the sensor unit 33. The determination of the movement information takes place, for example, additionally dependent upon a pre-determined target position. In other words, the determining unit 8 is configured to determine the movement information dependent upon the aforementioned relative position and the target position. The target position corresponds, for example, to the pre-determined trajectory 11. The target position may be stored in the determining unit 8. For example, the target position, which is stored in the determining unit 8, is related to the reference position.

Referring again to FIG. 1, the immovable module 15 may have a sensor unit 12. The sensor unit 12 may have a camera, an electromagnetic sensor, an ultrasonic sensor, a radar sensor, or an X-ray sensor. The camera may be part of an optical tracking system, such as is well known from the prior art. The electromagnetic sensor may be part of an electromagnetic tracking system, such as is well known from the prior art. The sensor unit 12 is configured to determine the position of the positioning unit 1 relative to the module 15.

The determining unit 13 is configured to determine the movement information dependent upon the relative position between the positioning unit 1 and the immovable module 15. The determination of the movement information takes place (e.g., additionally) dependent upon the pre-determined target position. In other words, the determining unit 8 is configured to determine the movement information dependent upon the aforementioned relative position and the target position.

The acquisition unit 5 may be configured to receive the movement information exclusively from the determining unit 8. Alternatively, the acquisition unit may be configured to receive the movement information exclusively from the determining unit 13. Alternatively, the acquisition unit 5 may be configured to receive the movement information both from the determining unit 8 and also from the determining unit 13. The reception of the movement information from the determining unit 13, which is arranged in the immovable module 15, takes place, for example, via radio (e.g., by Wi-Fi or Bluetooth).

Each determining unit 8, 13 is configured to determine the movement information such that during a visualization of the movement information, the positioning unit 1 is guided in the direction of the pre-determined trajectory 11. In other words, the movement information may indicate the direction in which the positioning unit 1 is to move in order to arrive in the direction of the pre-determined trajectory or into alignment with the pre-determined trajectory 11. For this purpose, a mathematical rule and/or an allocation table may be provided.

In a further embodiment, the positioning system 9 may have a registration unit 14. The registration unit 14 is configured to acquire the positioning of the positioning unit 1 on the medical object 6. For this purpose, the registration unit 14 may have a camera. Alternatively, the registration unit 14 is configured to receive a corresponding image of the positioning unit 1 arranged on the medical object 6 from the sensor unit 12. For example, the registration unit 14 is configured to determine, from the positioning of the positioning unit 1 on the medical object 6, a relative position between the positioning unit 1 and the medical object 6. These relative positions may be used during determination of the relative position between the medical object 6 and the sensor unit 12 or the module 15. In other words, the relative position between the positioning unit 1 and the medical object 6 is to be taken into account for the determination of the relative position between the medical object 6 and the sensor unit 12 or the module 15. Alternatively or additionally, the determining unit 8, 13 is configured to take account of the relative position between the positioning unit 1 and the medical object 6 for the determination of the movement information.

Figure 4:
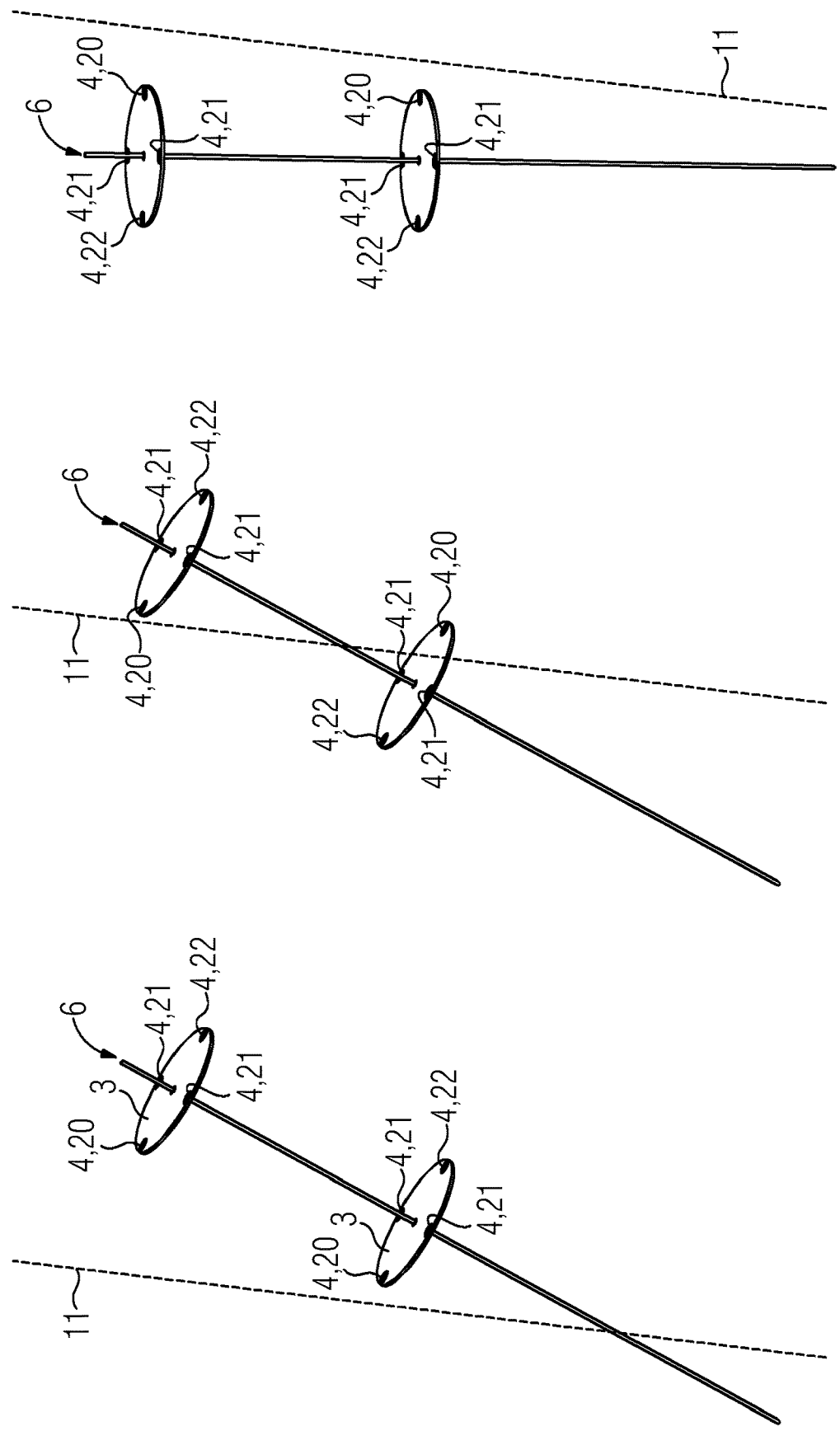
FIG. 4 shows a schematic perspective view showing an overview of a visualization of an item of movement information through the positioning unit.

FIG. 4 shows, by way of example, how the indicators 4 may be controlled according to the movement information. Thereby, the control of the indicators 4 takes place dependent upon the position and/or orientation of the positioning unit 1 relative to the pre-determined trajectory 11. Indicators 4 arranged in a spatial direction on the indicating element 3 in which the positioning unit 1 is to be moved, presents a first light pattern 20. For example, the first light pattern 20 includes the representation of a first color value and/or a blinking. In other words, according to the movement information, the positioning unit 1 is to be moved in the direction of the aforementioned spatial direction in order to reach the pre-determined trajectory 11. Indicators 4 that lie in this spatial direction show the first light pattern 20. Indicators 4 arranged opposing this spatial direction on the indicating element 3 present a third light pattern 22. For example, the third light pattern 22 includes the representation of a third color value and/or a blinking.

Indicators 4 arranged on the indicating element 3 according to a spatial direction along which, according to the movement information, no movement is provided present a second light pattern 21. The second light pattern 21 includes, for example, the representation of a second color value and/or a blinking.

The respective blinking of the different light patterns 20, 21, 22 may differentiate the light patterns. Alternatively or additionally, the first color value, the second color value and the third color value may differ from one another. For example, the first color value corresponds to a blue color, the second color value corresponds to a green color, and the third color value corresponds to a red color.

Figure 5:
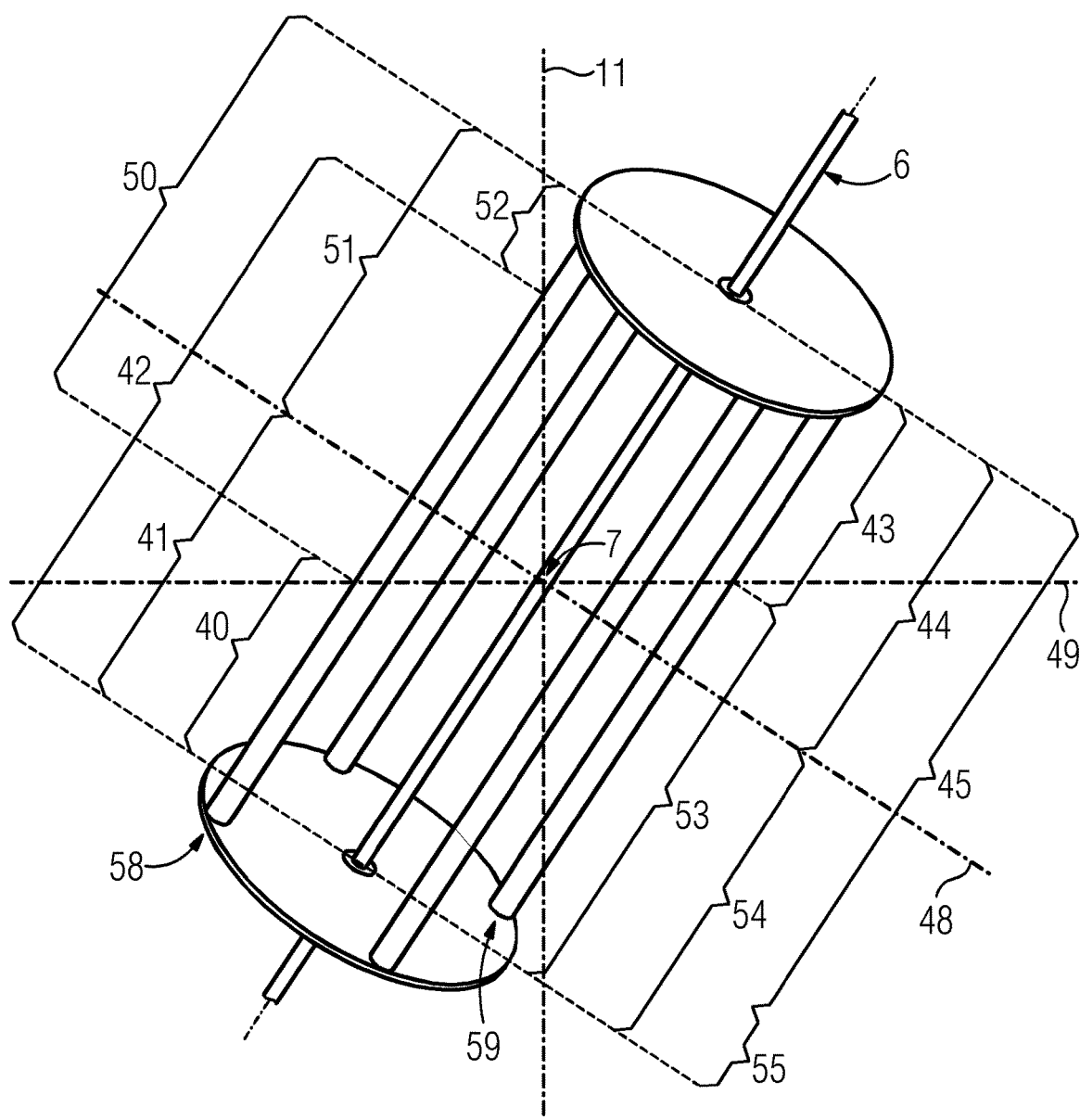
FIG. 5 shows a schematic perspective view showing an overview of an alternative visualization of an item of movement information through the positioning unit.

According to FIG. 5, the control of the linear lights 32 takes place in an analogue manner. Due to the continuous form of the linear lights 32, however, a different control of the linear lights 32 according to the movement information may be provided. For two of the linear lights 58 and 59, the control is represented according to different exemplary embodiments. Respective regions of the linear lights 58, 59 are to be moved, by way of example, in the drawing plane to the left through to the far right, in order to be guided in the direction of the trajectory 11 according to the movement information. For this reason, the linear lights 58, 59 represent different light patterns in some portions. Above an intersection point 47 between the medical object 6 and the trajectory 11, the positioning unit 1 is to be moved to the left. Below the intersection point 47, the positioning unit 1 is to be moved to the right.

First example: An imaginary horizontal line 49 may be drawn through the intersection point 47. Situated above this line 49 is a region 50 of the linear light 58 that is controlled for representing a first light pattern. Situated below the line 49 is a region 40 that is controlled for representing a second, different light pattern. Situated above the line 49 is a region 43 of the linear light 59 that is controlled for representing the second light pattern. Situated below the line 49 is a region 53 of the linear light 59 that is controlled for representing the first light pattern.

Second example: An imaginary line 48 may be drawn through the intersection point 47, perpendicular to the main extent direction of the medical object 6. Situated above this line 48 is a region 51 of the linear light 58 that is controlled for representing the first light pattern. Situated below the line 48 is a region 41 that is controlled for representing the second light pattern. Situated above the line 48 is a region 44 of the linear light 59 that is controlled for representing the second light pattern. Situated below the line 48 is a region 54 of the linear light 59 that is controlled for representing the first light pattern.

Third example: Situated above the trajectory 11 is a region 52 of the linear light 58 that is controlled for representing the first light pattern. Situated below the trajectory 11 is a region 42 that is controlled for representing the second light pattern. Situated above the trajectory 11 is a region 45 of the linear light 59 that is controlled for representing the second light pattern. Situated below the trajectory 11 is a region 55 of the linear light 59 that is controlled for representing the first light pattern.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A positioning unit for guiding a medical object, the positioning unit comprising:
  a securing unit, by which the positioning unit is arrangeable on the medical object;
  an indicating element that is arranged in a fixed position relative to the securing unit, the indicating element comprising:
    two plates that are each arrangeable on the medical object by a respective part of the securing unit independently of one another, and
    a plurality of indicators, wherein at least three first indicators of the plurality of indicators are arranged on a first of the two plates, and at least three second indicators of the plurality of indicators are arranged on a second of the two plates, and wherein the securing unit is arrangeable on the medical object such that the medical object extends through the first plate between one of the at least three first indicators and another of the at least three first indicators and through the second plate between one of the at least three second indicators and another of the at least three second indicators; and
  an acquisition unit for acquiring an item of movement information,
  wherein the positioning unit is configured to control the plurality of indicators dependent upon item of the movement information.

2. The positioning unit of claim 1, wherein the medical object is a needle.

3. The positioning unit of claim 1, wherein the two plates are round plates.

4. The positioning unit of claim 1, wherein each indicator of the plurality of indicators is configured as a lighting device.

5. The positioning unit of claim 4, wherein the lighting device is a light-emitting diode.

6. The positioning unit of claim 1, wherein the plurality of indicators are arranged such that the plurality of indicators lie on a same circle or a same envelope surface of a cylinder.

7. The positioning unit of claim 6, wherein the securing unit is configured to arrange the positioning unit on the medical object such that a line of gravity, which extends along a main extent direction of the medical object, extends through a midpoint of the circle or the envelope surface.

8. The positioning unit of claim 6, wherein two adjacent items of the plurality of indicators that are arranged together on the circle or on the cylinder each have an even spacing from one another in a peripheral direction.

9. The positioning unit of claim 1, wherein the indicating element further comprises a plurality of linear lights,
  wherein the plurality of indicators are part of the plurality of linear lights, and
  wherein the securing unit is configured to arrange the positioning unit on the medical object such that the plurality of linear lights extend parallel to a main extent of the medical object.

10. The positioning unit of claim 1, wherein the positioning unit is configured, through corresponding control of the plurality of indicators, to indicate a direction in which the positioning unit is to be turned, moved, or turned and moved according to the item of movement information.

11. The positioning unit of claim 1, wherein the positioning unit is configured to:
  in a first illumination step, indicate a direction in which the positioning unit is to be turned according to the item of movement information; and
  in a second illumination step, indicate the direction in which the positioning unit is to be moved according to the item of movement information, and
  wherein the first illumination step and the second illumination step take place one after the other.

12. The positioning unit of claim 1, wherein the positioning unit is configured, through corresponding control of the plurality of indicators, to indicate simultaneously for at least two subregions along a main extent direction of the positioning unit a direction in which a relevant subregion of the at least two subregions is to be turned, moved, or turned and moved according to the item of movement information.

13. The positioning unit of claim 1, wherein the at least three first indicators comprise four first indicators arranged on the first plate, and the at least three second indicators comprise four second indicators arranged on the second plate.

14. The positioning unit of claim 1, wherein the item of movement information includes a translation of the positioning unit.

15. The positioning unit of claim 1, wherein the positioning unit is arrangeable on the medical object, via the securing unit, such that the first plate is at a distance away from the second plate along the medical object and the first plate and the second plate are physically connected to each other only indirectly via the medical object.

16. A positioning system comprising:
a positioning unit for guiding a medical object, the positioning unit comprising:
 a securing unit, by which the positioning unit is arrangeable on the medical object;
 an indicating element that is arranged in a fixed position relative to the securing unit, the indicating element comprising:
  two plates that are each arrangeable on the medical object by a respective part of the securing unit independently of one another, and
  a plurality of indicators, wherein at least three first indicators of the plurality of indicators are arranged on a first of the two plates, and at least three second indicators of the plurality of indicators are arranged on a second of the two plates, and wherein the securing unit is arrangeable on the medical object such that the medical object extends through the first plate between one of the at least three first indicators and another of the at least three first indicators and through the second plate between one of the at least three second indicators and another of the at least three second indicators; and
an acquisition unit for acquiring an item of movement information, wherein the positioning unit is configured to control the plurality of indicators dependent upon the item of movement information;
a sensor unit configured to acquire a position, orientation, or position and orientation of the positioning unit; and
a processor configured to determine the movement information dependent upon the acquired position, orientation, or position and orientation of the positioning unit and a target position.

17. The positioning system of claim 16, further comprising a registration unit configured to acquire a positioning of the positioning unit on the medical object.

18. The positioning system of claim 16, wherein the sensor unit comprises an acceleration sensor that is arranged on the positioning unit, and the sensor unit is configured to determine the position, orientation, or position and orientation of the positioning unit based on acceleration data of the acceleration sensor.

19. The positioning system of claim 16, wherein the sensor unit comprises an ultrasound sensor, a radar sensor, an X-ray sensor, an electromagnetic sensor, or a camera.

20. The positioning system of claim 16, wherein the sensor unit is configured to acquire the position or the position and the orientation of the positioning unit.

* * * * *